United States Patent [19]
Cryberg et al.

[11] Patent Number: 4,528,400
[45] Date of Patent: Jul. 9, 1985

[54] PREPARATION OF KETONES

[75] Inventors: Richard L. Cryberg, Chardon; Russell M. Bimber, Painesville, both of Ohio

[73] Assignee: SDS Biotech Corporation, Painesville, Ohio

[21] Appl. No.: 323,262

[22] Filed: Nov. 20, 1981

Related U.S. Application Data

[63] Continuation-in-part of Ser. No. 159,309, Jun. 9, 1980, abandoned, which is a continuation of Ser. No. 876,334, Feb. 9, 1978, abandoned, which is a continuation of Ser. No. 716,142, Aug. 20, 1976, abandoned.

[51] Int. Cl.$^3$ ............................................. C07C 45/48
[52] U.S. Cl. .................................... 568/314; 568/346; 568/388; 568/390; 568/391; 568/345; 568/347; 568/313; 568/315; 502/304; 502/312; 502/353
[58] Field of Search ............... 568/397, 312, 313, 314, 568/315, 346, 388, 390, 391, 345, 347

[56] References Cited

U.S. PATENT DOCUMENTS

| | | | |
|---|---|---|---|
| 2,612,524 | 9/1952 | Zellemoyer et al. | 568/397 |
| 2,697,729 | 12/1954 | Ohlson et al. | 568/397 |
| 3,075,016 | 1/1963 | Hammerberg et al. | 568/397 |
| 3,466,333 | 9/1969 | Young et al. | 568/397 |
| 3,574,703 | 4/1971 | Hogemeyer et al. | 568/397 |
| 4,224,252 | 9/1980 | Kyo et al. | 568/388 |

OTHER PUBLICATIONS

Thermal Behavior of Aliphatic and Alicyclic Ketones, Furukawa and Naruchi, Nihon Kagaku Zasshi (Journal of the Chemical Society of Japan, Pure Chemistry Section), vol. 87, No. 10, (1966), pp. 1108–1110, (102–104).

Primary Examiner—James H. Reamer
Attorney, Agent, or Firm—John P. Hazzard; John J. Freer

[57] ABSTRACT

Disclosed is a method for the preparation of ketones by a catalytic vapor phase reaction of using reactants such as ketones with carboxylic acids and/or carboxylic acid precursors. An example of such a reaction is that of acetone with pivalic acid over a ceria-alumina catalyst at a temperature of nearly 470° C. to produce pinacolone.

18 Claims, No Drawings

PREPARATION OF KETONES

BACKGROUND OF THE INVENTION

This application is a continuation-in-part of copending U.S. application Ser. No. 159,309, filed June 9, 1980, now abandoned which prior application was in turn a continuation of prior application Ser. No. 876,334, filed Feb. 9, 1978, now abandoned, which was a continuation of original application Ser. No. 716,142, filed Aug. 20, 1976, now abandoned.

The present invention relates generally to a method for preparing ketones using reactants such as ketones and carboxylic acids. In one embodiment, it relates to an entirely new process for the production of unsymmetrical ketones from ketones and carboxylic acids over a ceria-alumina catalyst system in the temperature range of 300° to 550° C. utilizing a very short contact time over the catalyst to achieve a conversion in the range of 85 percent or more while recovering most of the unconverted reactants for recycling. An excellent example of such a reaction is the reaction of acetone with pivalic acid over a ceria-alumina catalyst to produce pinacolone.

Pinacolone is an intermediate which is useful in the preparation of pharmaceutical products and pesticides for which improved methods of manufacture have been sought for some time now. An electrolytic reductive coupling of acetone to form pinacol which can be converted to pinacolone has been carried out on an experimental basis for a number of years to produce small quantities of pinacol, but such processes have thus far failed to receive much commercial utilization because of the cost factors involved in these methods.

A thermo-chemical route as taught by literature utilizes a pyrolysis of one or two carboxylic acids to yield symmetrical or unsymmetrical ketones, respectively. This type of reaction has been used commercially with the significant disadvantage that the raw materials used in the manufacture of the ketones are costly because the selectivity of the reaction to unsymmetrical ketones is low.

The article *Thermal Behavior of Aliphatic and Alicyclic Ketones*, J. Chem. Soc. Japan, Vol. 87, No. 10 (1966) pp. 1108–1110 by Furukawa and Naruchi describes observations of work done in the study of the thermal decomposition of ketones. In the course of this work, ketones were reacted together at 500° C. in the presence of calcium carbonate. The authors do not show the production of ketones from a ketone and a carboxylic acid or carboxylic acid precursor nor do they show any recycle features. This article may tend to indicate the possibility of "equilibrating" two symmetric ketones to form an unsymmetrical ketone and the possibility of "equilibrating" an unsymmetric ketone to two different symmetric ketone, but the discussion on p. 10 (English translation) indicates that this is not the case.

Therefore, as with all chemical processes, it would be very desirable to be able to reduce the cost of a thermochemical route to the pinacolone or other ketones for use in the chemical industry on a commercial basis.

SUMMARY OF THE INVENTION

It is therefore an object of the present invention to provide a method for the preparation of ketones from ketones and carboxylic acids so as to produce a high yield of the ketone while lowering the overall cost of capital investment and raw materials used in such a process. Another object of the present invention is the providing of a recycling system to provide high yields of wanted products at the expense of unwanted by-products.

It is a further object of the present invention to provide a catalyst system for promoting such novel chemical reactions within the range of commercial utilization.

These and other objects of the present invention, and the advantages thereof over the prior art forms, will become apparent to those skilled in the art from the detailed disclosure of the present invention as set forth hereinbelow.

A method has been found for the production of ketones comprising the steps of: introducing a ketone and a carboxylic acid into a chamber; passing the mixture of the ketone and the carboxylic acid over a heated catalytically active material; and recovering the ketone.

It has also been found that unsymmetrical ketones can be produced by: mixing a ketone and a carboxylic acid; passing the mixture through a catalyst bed consisting essentially of a ceria-compound on an alumina support; and recovering the unsymmetrical ketone.

It has also been found that an unsymmetrical ketone may be produced by: mixing two different symmetrical ketones; passing the mixture through a catalyst bed consisting essentially of a ceria-compound on an alumina support; and recovering the unsymmetrical ketone.

DESCRIPTION OF THE PREFERRED EMBODIMENTS

In one important embodiment, unsymmetrical ketones may be produced according to the general reaction: (I) $R_2CO + 2R'CO_2H$ to yield $2RR'CO + CO_2 + H_2O$ wherein R is a hydrocarbon radical and R' is a hydrocarbon radical other than R. The acid reactant in the general reaction (I) may be cyclic, acyclic or aromatic as well as monocarboxylic or dicarboxylic. In the presently preferred embodiment, cyclic monocarboxylic acids are preferred. This reaction has been found to occur over catalytically active materials with a relatively short contact time in a temperature range of 300° to 550° C. Unsymmetrical ketones resulting from the above-cited reaction can be recovered in yields up to 80 percent or more. Groups representative of R and R' in the above-cited starting materials would include aliphatic groups such as methyl, ethyl, propyl, isopropyl, t-butyl, pentyl, hexyl, and benzyl, as well as aromatic substituents such as phenyl, p-tolyl and naphthyl.

In each specific case, conditions may need to be altered slightly to maximize yields. For example, acetone and pivalic acid react over a ceria-alumina catalyst at a temperature near 470° C. to produce pinacolone. When using a two:one molar ratio of acetone:pivalic acid with a ten second contact time, the conversion of the pivalic acid to pinacolone was in the range of 80 percent of theoretical.

As another important feature of the present invention, most of the unconverted reactants in this novel chemistry can be recovered and refed into the reactor zone to accomplish higher yields. For example, by recycling the acetone and pivalic acid reactants above, virtually 100 percent yields are possible. This results in about two moles of pinacolone being produced per every one mole of acetone consumed.

It is thought that the above-described acetone and pivalic acid reaction to obtain pinacolone proceed as follows:

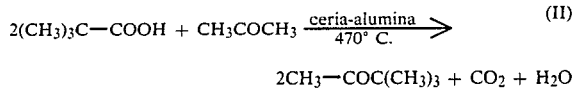

$$2(CH_3)_3C\!-\!COOH + CH_3COCH_3 \xrightarrow[470° C.]{\text{ceria-alumina}}$$

$$2CH_3\!-\!COC(CH_3)_3 + CO_2 + H_2O \quad (II)$$

It will be noticed that two moles of the pivalic acid combine with one mole of the acetone to provide two moles of pinacolone. Although not wanting to be bound to any particular theory, it is believed that the pivalic acid forms a complex with the ceria-alumina catalyst system by losing the acidic hydrogen atom off of the pivalic acid. Thereafter, the carbon to oxygen double bond is attacked by the methylene anion of the acetone to provide a shift of electrons to the oxygen atom and the loss of an oxygen atom with the coupling of the acetone by its methyl group thereto. This results in a probable intermediate of the formula $(CH_3)_3CCOCH_2COCH_3$. It is believed then that this intermediate is hydrolyzed causing a cleavage which results in pinacolone and an acetic acid group leaving which will thereafter react with a second complexed pivalic acid group to form more pinacolone. In this process, carbon dioxide and water are also formed.

Further examples of ketones produced from ketones and carboxylic acids include: acetone and benzoic acid to obtain acetophenone; acetone and propionic acid to obtain methyl ethyl ketone and diethyl ketone; acetone and phenylacetic acid to obtain phenylacetone; diethyl ketone and acetic acid to obtain acetone and methyl ethyl ketone; diethyl ketone and benzoic acid to obtain propiophenone; benzophenone and acetic acid to obtain acetophenone; and benzoic acid and methyl ethyl ketone to obtain acetophenone and propiophenone.

Although the carboxylic acid reactant is preferred in reaction (I), carboxylic acid precursors have also been found to be useful. For example, it has been found that benzyl alcohol or benzaldehyde may be substituted for benzoic acid in the reaction with acetone to obtain acetophenone. Further examples include, acetone and dimethyl succinate to obtain 2,5-hexandione; acetone and dimethyl terephthalate to obtain p-diacetylbenzene, and acetone and methyl pivalate to obtain pinacolone. Thus, carboxylic acid precursors include alcohols, esters, nitriles, anhydrides, aldehydes and alkyl ammonium salts having from one to three alkyl groups of one or two carbon atoms each. Mixtures of such carboxylic acid precursors including mixtures containing carboxylic acids as well as mixtures of carboxylic acids with themselves are contemplated. Although not wanting to be bound to any particular theory, it is believed that reactions using the aldehyde or alcohol for a starting material proceed by an oxidation-reduction disproportionation of the feedstocks.

It has also been found that the present invention can be useful for rearrangements of ketones by themselves such as methyl ethyl ketone alone to obtain acetone and diethyl ketone and acetone and diethyl ketone to obtain methyl ethyl ketone.

This invention will be useful in reactions like: benzophenone and pivalic acid to obtain t-butyl phenyl ketone; 1,3-dichloroacetone and pivalic acid to obtain monochloropinacolone; and cyclopentanone and acetic acid to obtain 2,7-octanedione.

It is also contemplated that the present invention will provide good activity for other reactions falling within other general types, such as: (III) $RCH_3 + R^1CO_2H$ to yield $RCH_2COR^1$, where R is an election withdrawing group such as 2 or 4 pyridyl and $R^1$ is alkyl or aryl.

Moreover, it is further contemplated that with yet additional reactants, good activity may be obtained for yet other reactions, while following the instant invention parameters, such as, for example: (IV) $RCH_2X + CH_3COCH_3$ to yield $RCH_2CH_2COCH_3 + HX$, where R is an activating group such as hydrogen, alkyl or aryl and X is a good leaving group such as a halogen.

All of the above-cited reactions take place by passing the vapors of the reactants over heated catalytically active materials. Suitable materials include iron filings, alumina, manganous oxides, thoria and ceria types of catalysts. The preferred catalyst system, from experience, is a ceria compound deposited on an alumina, silica or carbon support.

One specific catalyst is exemplified by a cerium acetate converted to ceria on an alumina support and as such a good activity will be produced if the ceria concentration is in the range of 1 to 10 percent calculated as $CeO_2$ to total weight. The amount used will depend upon the specific surface area presented by the alumina support. Where the support used is alumina available from Harshaw Chemical Company under the trademark of Harshaw Al 1404 T-1/8 ®, the specific area being approximately 190 square meters per gram, the range of ceria is preferably 5 to 10 percent. A slight aging of the catalyst has been found during initial use, as is usual with such catalyst systems. Thereafter, this system will provide good activity of a steady nature for time periods in excess of 1000 hours of use. The ceria-alumina catalyst provides a distinct practical advantage of thoria catalysts because the ceria is not radioactive, thus eliminating a hazard of thoria and the inconvenience of Nuclear Regulatory Commission licensing and regulations covering its use. Other specific catalysts are discussed in greater detail hereinbelow in connection with the examples.

This novel process of the instant invention will provide a distinct economic advantage over prior methods, particularly for production of pinacolone over either the mixed acid pyrolysis route or the formation of the mixed anhydrides and subsequent pyrolysis to the ketones. Lower capital and operating costs are expected in the process of the present invention versus that of the mixed acid pyrolysis because the heat of vaporization of acetone is less than that of acetic acid, thus requiring less energy. This is increased by the fact that one mole of acetone is equal to two moles of acetic acid used in the old methods. Further, about one-half as much carbon dioxide and water are produced, making it easier to condense and recover the product and unreacted materials. There is also less dilution of the reaction mixture with by-product carbon dioxide and water so that a reaction vessel only two-thirds to three-quarters as large as that used in the acid pyrolysis route may be used to result in a savings in the cost of catalyst and reactor. In addition, smaller condensers with lower energy requirements will be adequate.

However, it should be understood that additives in minor amounts that find utility in catalytic reactions are contemplated for use with the reactants, for example, water used as a desorption agent may be used.

In order that those skilled in the art may more readily understand the present invention and certain preferred aspects by which it may be practiced, the following specific examples are afforded to show the methods of preparation of various products.

EXAMPLE 1

An apparatus suitable for use in the above-described reactions was assembled having a vertical tube furnace constructed over Pyrex tubing for heating the reaction zone. The reaction tube contained a thermowell in the reaction zone to obtain accurate temperature readings. The upper section was packed with glass beads where the reactants were heated up to reaction temperature while the lower section contained a smaller heating segment to sustain these temperatures. The preheater was thermostatically controlled to provide more heat when reactants were being fed into the section to maintain the temperature. The catalyst should be positioned between the glass beads of the preheater and glass beads near the outlet of the lower section so that it begins just below upper section and runs down approxiamtely 75 percent of the length of the lower section and between the concentric thermowell and the glass that contains the reactor. The reactor was connected by means of a "Y" tube to a condensate receiver on the bottom and two water-cooled condensers in series on the vertically straight neck. For example, the lower condenser may be of a six-bulb Allihn type and the upper one of the Friedrich's type. Also, it might be desirable to use a feed reservoir on a triple beam balance connected to a metering pump to feed the reactants to the system at a known rate. With a "Y" tube connected to the upper section of the tube furance, the reactants may be fed into one branch and a thermocouple well placed in the other branch for measuring temperatures.

A thoria catalyst was prepared from 40 grams of thorium nitrate tetrahydrate [Th(NO$_3$)$_4$. 4H$_2$O] in water, impregnated on 200 ml. or 172 grams of alumina available as Harshaw Alumina catalyst Al 1404 T-1/8 ®. The wetted alumina was stripped of water in a rotary evaporator under aspirator vacuum. This was transferred to a large porcelain dish where it was heated strongly while aspirating the NO$_x$ from it through a water trap. The resulting loose material was then placed into the reactor tube with glass beads ahead and behind the catalyst zone.

The system was then flushed out with acetone vapors to clear the system of any residues and the catalyst temperature gradually rose to 440° to 485° C. The feed reservoir was changed from acetone to a 2:1 molar ratio of acetone:pivalic acid. The condensate samples removed were composed of 4 to 5 parts red organic layer over a colorless aqueous layer. Product purification and gas chromatographic studies of the organic layer showed the presence of pinacolone in yields ranging as high as 90 percent of theoretical on a single pass. Recovery of reactants and recycling can achieve even higher yields.

EXAMPLE 2

A ceria catalyst was prepared from 100 grams of cerium acetate hydrate [CE(OAc)$_3$.XH$_2$O] and 400 ml. of water at room temperature with agitation to dissolve nearly all of the material. The solution was filtered and rinsed with several portions of water to result in approximately 460 ml. of filtrate. The solution was then combined with 1050 grams of Harshaw Alumina catalyst Al 1404 1/8 ® and tumbled in a gallon jug. The solution was absorbed to leave no freely pourable liquid and thus wetting the alumina. The mixture was dried in a procelain dish at approximately 200° C. for 15 hours and then installed in the apparatus according to Example 1.

The system was flushed out according to Example 1 and the feed reservoir charged with a 2:1 molar ratio of acetone:pivalic acid. Pinacolone product was recovered from the condensate in yields up to 90 percent of theoretical as evidenced by gas chromatographic studies.

EXAMPLES 3-15

Using the apparatus of Example 1 and the catalyst of Example 2, other reactions can be performed in a fashion similar to Examples 1 and 2. In each case, the reaction products were confirmed by mass spectra and quantitatively measured by gas chromatographic studies. These reactions are summarized in the following Table 1. The Molar Ratio refers to the ratio of the reactants in the order stated in the feed reservoir. With the exception of the pinacolone, no effort was made to maximize the yields.

TABLE I

| Ex. No. | Reactants | Reaction Temp. °C. | Molar Ratio | % Yield of Products |
|---|---|---|---|---|
| 3 | benzoic acid: acetone | 420-440 | 1:33 | 25 acetophenone |
| 4 | acetone: propionic acid | 430 | 1:1 | 38 methyl ethyl ketone 52 diethyl ketone |
| 5 | acetone:dimethyl succinate | 470 | 3:1 | 2 2,5-hexandione |
| 6 | acetone:phenyl-acetic acid | 430-455 | 4:1 | 60 phenylacetone |
| 7 | diethyl ketone: acetic acid | 420-440 | 1:1 | 40 acetone 55 methyl ethyl ketone |
| 8 | diethyl ketone: benzoic acid | 430-480 | 4:1 | 8 propiophenone |
| 9 | benzophenone: acetic acid | 430-480 | 1:5 | 7 acetophenone |
| 10 | benzoic acid: methyl ethyl ketone | 450 | 1:4 | 21 acetophenone 17 propiophenone |
| 11 | methyl ethyl ketone | 400 | — | 6 acetone 12 diethyl ketone |
| 12 | acetone:diethyl ketone | 440-500 | 1:1 | 14 methyl ethyl ketone |
| 13 | acetone:dimethyl terephthalate | 440-460 | 40:1 | 2 p-diacetyl-benzene |
| 14 | acetone: benzaldehyde | 480-490 | 2:1 | 25 acetophenone |
| 15 | acetone:benzyl alcohol:water | 480-485 | 2:1:2 | 5 acetophenone |

EXAMPLES 16-18

These examples show the use of alternative forms of the acid component of pivalic acid are also suitable for producing pinacolone:

An apparatus suitable for use in the above-described reactions was assembled having a vertical tube furnace for heating the reaction tube. The furnace was constructed around a pyrex reaction tube having a 2.5 cm O.D., a 2.2 cm I.D. and a length of 75 cm. The reaction tube contained a concentric pyrex thermocouple well having a 0.8 cm O.D., the actual volume of the reaction zone of the reaction tube being approximately 116 ml. The reaction tube consisted of an upper section where the reactants enter containing a preheater segment to bring the reactants up to temperature while the lower section contains a second heating segment to sustain these temperatures. The catalyst was positioned between glass beads so that it occupied 38 cm of the center of the reaction tube with approximately 18 cm of glass beads on each end of said tube. The reactor was connectd to a condensate receiver under the reactor tube and the vapor rose through two efficient water-cooled condensers in series to ensure that the reaction products were rinsed down into said receiver. This condensate receiver was a two-necked, 250 ml round bottom glass flask.

The catalyst was $CeO_2$ impregnated on alumina prepared from a filtered saturated aqueous solution of cerium acetate containing a trace of acetic acid deposited on Harshaw alumina Al 1404 T-1/8 ® and oven dried at 100° C. overnight. The resulting loose material was then placed into the reactor tube (occupying approxiamtely 38 cm in the center of the tube) with glass beads on each end (occupying approxiamtely 18 cm on each end of said tube) resulting in approximately 3 percent by weight $CeO_2$ being present in the reaction tube.

The system was flushed with acetone by feeding acetone at a rate of one ml per minute (ml/min) using a metering pump. The preheating zone was gradually brought to 470° C. and the reaction zone gradually brought to 475° C. by the use of variacs. The feed was changed from acetone to the various reactants at the molar ratios set out in Table II below. The condensate product samples were collected in the condensate reservoir and analyzed using gas chromatography and gas chromatography/mass spectroscopy to prove the identity of the products.

The system was not optimized for each reaction and, therefore, yields were not determined; however, yields of approximately ninety percent or higher should be possible with proper optimization.

TABLE II

| Ex. No. | Reactants | Reaction Temperature (°C.) | Molar Ratio | Product |
| --- | --- | --- | --- | --- |
| 16 | Methyl pivalate:acetone | 475 | 1:2.05 | Pinacolone |
| 17 | Pivalonitrile:acetone | 475 | 1:1.46 | Pinacolone |
| 18 | Trimethylammonium pivalate:acetone | 475 | 1:3.75 | Pinacolone |

EXAMPLE 19

This example shows that other acids may be used in place of pivalic acid in this novel chemistry.

Using the apparatus, catalyst and method of Examples 16–18, cyclohexane carboxylic acid and acetone in a molar ratio of 1:2.76 was introduced into the system after purging with acetone. Methyl cyclohexyl ketone was produced and identified as in Examples 16–18.

EXAMPLE 20

This example illustrates the applicability of using non-pivalic acid, acid precursors.

Again using the apparatus, catalyst and methods of Examples 16–18, acetonitrile and diethyl ketone in a 1:1 molar ratio were introduced into the system after purging with acetone. Methyl ethyl ketone was produced and identified as in Examples 16–18.

EXAMPLE 21

This example illustrates the applicability of recycling a mixture of product and unreacted starting materials to increase the product yield.

Using the apparatus, catalyst and method of Examples 16–18, acetone and diethyl ketone in approximately 1:1 molar ratio were introduced into the system. Three distillation cuts of the reaction product were isolated. The second cut contained mostly the methyl ethyl ketone product. The first cut being from 25° C. to 70° C. and containing mostly unreacted acetone and the third cut being above 86° C. and containing mostly unreacted diethyl ketone. These two cuts were combined and gas chromatographic analysis revealed 1.4 percent methyl ethyl ketone. This combined material was thus recycled through the apparatus and collected as described above. Gas chromatographic analysis revealed a methyl ethyl ketone yield of 2.8 percent.

The following examples illustrate the use of various suitable catalysts and catalyst supports.

EXAMPLE 22

A ceria catalyst was prepared from 21.5 g of cerium chloride hydrate ($CeCl_3.7H_2O$) and approximately 60 ml of water at room temperature with agitation to dissolve the cerium compound. To this solution 48.8 g of 6–14 mesh coconut charcoal was added and this mixture placed in a rotary evaporator. After evaporation of most of the liquid with repeated application and release of vacuum, the moist charcoal was dried overnight in an oven at 120° C. and then installed in the apparatus of Example I as disclosed in Example I.

The system was flushed out according to Example I and the feed reservoir charged with a 2:1 molar ratio of acetone:pivalic acid. Pinacolone product was recovered from the condensate as evidenced by gas chromatographic analysis.

EXAMPLE 23

A magnesia catalyst was prepared using 40.0 g of MgO dissolved in approximately 40 ml of water containing 14 g of acetic acid and impregnated onto 75 g of alumina (Harshaw Alumina Al 1404-T1/8 ") following the procedure of Example 22.

The system was flushed out according to Example I and the feed reservoir charged with a 2:1 molar ratio of acetone:pivalic acid. Pinacolone product was recovered from the condensate as evidenced by gas chromatographic analysis.

EXAMPLE 24

An iron oxide catalyst was prepared from 25.8 g of $FeCl_3$ and 85 ml of warm water with agitation to dissolve nearly all of the material. The solution was then impregnated onto 114 g of Harshaw Al 1404-18 ® following the procedure of Example 22. This material was dried in a porcelain dish overnight at 400° C. and then installed in the apparatus according to Example 1.

The system was flushed out according to Example I and the feed reservoir charged with a 2:1 molar ratio of acetone:pivalic acid. Pinacolone product was recovered from the condensate as evidenced by gas chromatographic analysis.

EXAMPLE 25

Using the method and apparatus of Example 1, pinacolone was produced from a 2:1 molar ratio of acetone:pivalic acid using a commercially available zirconia catalyst. This catalyst is sold as Harshaw Zr 0304-T-1/8 " catalyst and contains 98 percent zirconia and 2 percent alumina and has a surface area of 50 $m^2/g$. Production of pinacolone was confirmed by gas chromatography.

EXAMPLE 26

Using the method and apparatus of Example 1, pinacolone was produced from a 0.6:1 molar ratio of acetone:pivalic acid using a commercially available chromia catalyst. This catalyst is sold as Harshaw Cr 0304-T-1/8 ®" catalyst having a surface area of 120 m²/g. Production of pinacolone was confirmed by gas chromatography.

Thus, it should be readily apparent from the foregoing description of the preferred embodiments that the method hereinabove described accomplishes the objects of the invention and solves the problems attendant to the method of preparation of ketones.

What is claimed is:

1. A method for the production of product ketones comprising: introducing a reactant ketone and a carboxylic acid and/or carboxylic acid precursor into a chamber; passing the mixture of said reactant ketone and carboxylic acid and/or carboxylic acid precursor over a heated catalytically active metal oxide material; and recovering the product ketone.

2. A method according to claim 1 wherein the catalytically active metal oxide material is selected from the group consisting of oxides of cerium, thorium, iron, magnesium, chromium, zirconium and tungsten, preferably a ceria compound, on a support.

3. A method according to claim 2 wherein the support is alumina.

4. A method according to claim 1 wherein the temperature of reaction is in the range of 300° to 550° C.

5. A method according to claim 1 wherein the reaction contact time of the reactants and the catalytically active material is in the range of 0 to 60 seconds.

6. A method according to claim 1 wherein the ketone is acetone and the carboxylic acid is pivalic acid to yield pinacolone.

7. A method according to claim 1 wherein the ketone is acetone and the carboxylic acid is benzoic acid to yield acetophenone.

8. A method according to claim 1 wherein the ketone is acetone and the carboxylic acid is propionic acid to yield methyl ethyl ketone and diethyl ketone.

9. A method according to claim 1 wherein the ketone is acetone and the carboxylic acid precursor is dimethyl succinate to yield 2,5-hexanedione.

10. A method according to claim 1 wherein the ketone is acetone and the carboxylic acid is phenylacetic acid to yield phenylacetone.

11. A method according to claim 1 wherein the ketone is diethyl ketone and the carboxylic acid is acetic acid to yield methyl ethyl ketone.

12. A method according to claim 1 wherein the ketone is diethyl ketone and the carboxylic acid is benzoic acid to yield propiophenone.

13. A method according to claim 1 wherein the ketone is benzophenone and the carboxylic acid is acetic acid to yield acetophenone.

14. A method according to claim 1 wherein the ketone is acetone and the carboxylic acid precursor is dimethyl terephthalate to yield p-diacetylbenzene.

15. A method according to claim 1 wherein the ketone is acetone and the carboxylic acid precursor is selected from the group consisting of benzyl alcohol and benzaldehyde to yield acetophenone.

16. A method according to claim 1 wherein the ketone is acetone and the carboxylic acid precursor is methyl pivalate to yield pinacolone.

17. A method for the production of unsymmetrical ketones of the formula RR'CO where R is a hydrocarbon radical and R' is a hydrocarbon radical different from that of R comprising: introducing a ketone and a carboxylic acid and/or carboxylic acid precursor into a chamber; passing the mixture of said ketone and carboxylic acid and/or carboxylic acid precursor over a heated catalytically active metal oxide material; and recovering the unsymmetrical ketone.

18. A method as claimed in claims 1 or 17 wherein the reaction products are recycled through a catalyst bed, thereby improving the yield of the desired ketone or ketones.

* * * * *